US008140294B2

(12) United States Patent
Ramey et al.

(10) Patent No.: US 8,140,294 B2
(45) Date of Patent: Mar. 20, 2012

(54) TEMPERATURE ESTIMATIONS IN A BLOOD GLUCOSE MEASURING DEVICE

(75) Inventors: Blaine Edward Ramey, Indianapolis, IN (US); Michael L. Brown, Greenwood, IN (US); James L. Pauley, Jr., Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 424 days.

(21) Appl. No.: 12/479,212

(22) Filed: Jun. 5, 2009

(65) Prior Publication Data

US 2010/0307916 A1 Dec. 9, 2010

(51) Int. Cl.
*G01K 13/00* (2006.01)
(52) U.S. Cl. .......... 702/131; 702/99; 600/316; 600/347
(58) Field of Classification Search .................. 702/99, 702/130–136; 600/316, 347; 374/1
See application file for complete search history.

(56) References Cited

U.S. PATENT DOCUMENTS

| 5,405,511 A * | 4/1995 | White et al. ............... 205/777.5 |
| 6,349,269 B1 | 2/2002 | Wallace, Jr. | |

FOREIGN PATENT DOCUMENTS

| JP | 09159541 | 6/1997 |
| JP | 2007010317 | 1/2007 |
| WO | 2005000114 A2 | 1/2005 |

OTHER PUBLICATIONS

Blood Glucose Monitoring, http://en.wikipedia.org/wiki/Blood_glucose_monitoring, pp. 1-5, Feb. 26, 2009.
Glucose Meter, http://en.wikipedia.org/wiki/Blood_glucose_meter, pp. 1-7, Feb. 26, 2009.
Sofia, Electrical Thermal Resistance Measurements for Hybrids and Multi-Chip Packages, Analysis Tech, pp. 1-9, Wakefield, PA, USA.
Shabany, Component Size and Effective Thermal Conductivity of Printed Circuit Boards, Applied Thermal Technologies, LLC, pp. 489-494, Oct. 21, 2008, Santa Clara, CA, USA.
Bohm, et al., Compact Electro-Thermal Models of Semiconductor Devices with Multiple Heat Sources, 5th Int. Conf. on Thermal and Mechanical Simulation and Experiments in Micro-electronics and Micro-Systems, Euro SimE2004, 4 pages.
International Search Report, Appl. No. PCT/EP2010/003361, Mar. 2, 2011, 12 pages.

* cited by examiner

*Primary Examiner* — Manuel L Barbee
(74) *Attorney, Agent, or Firm* — Dinsmore & Shohl LLP (57) ABSTRACT

Methods of estimating the temperature of a reaction site on a measurement strip in a blood glucose measuring devices are provided. In one embodiment, a method includes determining an activation initiation time, an activation duration time, a thermal magnitude and a temperature elevation for heat generating components within a device. The temperature elevation for each of the heat generating components is determined at least in part by an impulse response matrix $[X_i]$, the activation initiation time, the activation duration time and the thermal magnitude for each of the heat generating components. The method further includes determining a total temperature elevation of the glucose measuring device by summing the temperature elevation of each of the heat generating components, reading a temperature value provided by the temperature measuring element, and determining a reaction site temperature estimation by subtracting the total temperature elevation from the temperature value provided by the temperature measuring element.

19 Claims, 5 Drawing Sheets

TEMPERATURE ESTIMATIONS IN A BLOOD GLUCOSE MEASURING DEVICE

TECHNICAL FIELD

The present invention generally relates to blood glucose measuring devices and, more particularly, devices and methods for estimating the temperature of a blood glucose reaction site.

BACKGROUND

As background, persons with diabetes suffer from either Type I or Type II diabetes in which the glucose level in the blood is not properly regulated by the body. As a consequence, many persons with diabetes often carry specialized electronic monitors, called blood glucose (bG) monitors, to periodically measure their glucose level and take appropriate action, such as administering insulin. Blood glucose monitors commonly comprise a base unit that houses control and test electronics required to test the glucose level in a sample of blood. Typical bG monitors may also have a measurement strip receptacle that accepts a disposable measurement strip. One end of the strip is inserted into the measurement strip receptacle while an exposed area contains a reaction site in which the user deposits a drop of blood, which is often obtained by pricking the skin with a lancet. Conductors run from the reaction site, which comprises various reagent chemicals, to the end inserted into base unit, thereby electrically coupling the reaction site to the control and test electronics. For blood glucose measurement results to be valid, the temperature at the reaction site must be within established lower and upper bounds. Therefore, an accurate temperature reading at the reaction site is desired to necessarily validate a blood glucose measurement. Due to the fact that all but the base of the bG test strip is exposed to ambient air, the reaction site temperature closely follows the ambient air temperature.

In addition to the bG monitor, persons with diabetes may also carry a portable electronic device, such as a cellular phone, smart phone, music player, personal digital assistant (PDA), or other similar devices. In order to reduce the number of electronic devices carried by persons with diabetes, there is a desire for integrating bG measuring functionality into another portable electronic device. For example, a bG monitor may be integrated into a cellular phone so that a diabetic only has to carry such a single, multi-functional device.

However, many portable devices generate significant internal heat resulting from active and passive components within the device, such as power supplies, resistors, integrated circuits, microcontrollers and the like. For example, the core temperature of a cellular phone can rise over 20 degrees Celsius above the ambient temperature during continuous use over a period of twenty minutes. Blood glucose monitors commonly rely on an internal temperature sensor to determine the temperature at the reaction site. Difficulties arise when the temperature reading provided by the internal temperature sensor changes not due to changes in the ambient air, but rather due to the internal heating of electronic components inside the device. Furthermore, the internal heat generation may vary depending on how the portable electronic device is being used. Because the internal temperature of such portable devices fluctuates greatly depending on device usage (e.g., cell phone talk times) and therefore influences the internal temperature, an internal temperature sensor maintained within the device is not capable of obtaining an accurate reaction site temperature to validate the blood glucose measurement.

Accordingly, a need exists for alternative temperature estimation methods and blood glucose measuring devices incorporating the same.

SUMMARY

According to one embodiment, a method of estimating the temperature of a reaction site on a measurement strip in a blood glucose measuring device having a plurality of heat generating components and a temperature measuring element is provided. The method includes determining an activation initiation time, an activation duration time, a thermal magnitude Qx and a temperature elevation Ex for each of the heat generating components. The temperature elevation Ex for each of the heat generating components is determined at least in part by an impulse response matrix $[X_i]$ for times $t_1$ through $t_{Nx}$, the activation initiation time, the activation duration time and the thermal magnitude Qx for each of the heat generating components. The method further includes determining a total temperature elevation $E_{total}$ of the glucose measuring device by summing the temperature elevation Ex of each of the heat generating components, reading a temperature value $T_{sensor}$ provided by the temperature measuring element, and determining a reaction site temperature estimation $T_{site}$ by subtracting the total temperature elevation $E_{total}$ from the temperature value $T_{sensor}$ provided by the temperature measuring element. The method further includes preventing a blood glucose test if the reaction site temperature estimation $T_{site}$ is greater than a maximum reaction site temperature $T_{max}$.

According to another embodiment, a blood glucose measuring device is provided. The blood glucose measuring device includes a plurality of heat generating components, a measurement strip port operable to receive a removable measurement strip having a reaction site for receiving a blood sample, and a temperature measuring element operable to measure an internal temperature of the blood glucose measuring device $T_{sensor}$ and to provide an internal temperature signal that corresponds with the measured internal temperature. The blood glucose measuring device further includes a controller operable to receive the internal temperature signal from the temperature measuring element and to determine a temperature estimate of the reaction site $T_{site}$ based on blood glucose measuring device usage by applying a dynamic thermal model. The dynamic thermal model determines a total temperature elevation $E_{total}$ based at least in part on an activation initiation time, an activation duration time and a thermal magnitude Qx of each heat generating component within a sample period. The controller calculates the temperature estimate of the reaction site $T_{site}$ by subtracting the total temperature elevation $E_{total}$ from the internal temperature $T_{sensor}$ provided by the internal temperature signal.

According to yet another embodiment, a blood glucose measuring device including a controller, a temperature measuring element, a measurement strip port, and a plurality of heat generating elements is provided. The measurement strip port is operable to receive a removable measurement strip having a reaction site positioned at an end. The temperature measuring element is in electrical communication with the controller and is operable to measure the temperature of the blood glucose measuring device and transmit a temperature signal corresponding to the temperature of the blood glucose measuring device to the controller. The controller is programmed to determine one or more activity characteristics within a sample period for each of the heat generating components, calculate a total temperature elevation within the blood glucose measuring device due to the activity characteristics of the heat generating elements within the sample period, and calculate a temperature estimation of the reaction site by subtracting the total temperature elevation from the temperature of the blood glucose measuring device corresponding to the temperature signal received from the temperature measuring element.

These and additional features provided by the embodiments of the present invention will be more fully understood in view of the following detailed description, in conjunction with the drawings.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

The embodiments described herein generally relate to portable electronic devices which are capable of measuring blood glucose (bG) levels in a blood sample provided by an individual with diabetes. More particularly, embodiments described herein relate to estimations of the temperature at a bG measurement strip reaction site when the reaction site may be at a different temperature than the temperature of the bG measurement electronic circuitry. Heat generating components within the bG measuring device (e.g., power sources, microcontrollers, resistors, etc.) may generate heat at varying levels depending on how the device is being used. It is desired to have an accurate estimation of the reaction site temperature to avoid unwarranted under or over-temperature lockout conditions that would prevent proper use of the bG measuring device.

Embodiments described herein utilize a dynamic thermal model that uses a temperature sensor reading to dynamically estimate the reaction site temperature depending on how the portable electronic device is being used. As described in detail herein, the dynamic thermal model of particular embodiments utilize the linear superposition of temperature elevation responses of a particular heat generating component over time to determine a total temperature elevation of the heat generating component. The dynamic thermal model further utilizes linear superposition of the total temperature elevations of each heat generating components to determine a total internal temperature elevation that may then be subtracted from the temperature reading provided by the temperature sensor. The dynamic thermal model takes into account activity characteristics of the portable electronic device such as an initiation time of when a component started generating heat, how long and at what thermal magnitude each component has been generating heat. In this manner, an estimation of the temperature of the reaction site on the measurement strip that takes into consideration device usage may be achieved.

Figure 1:
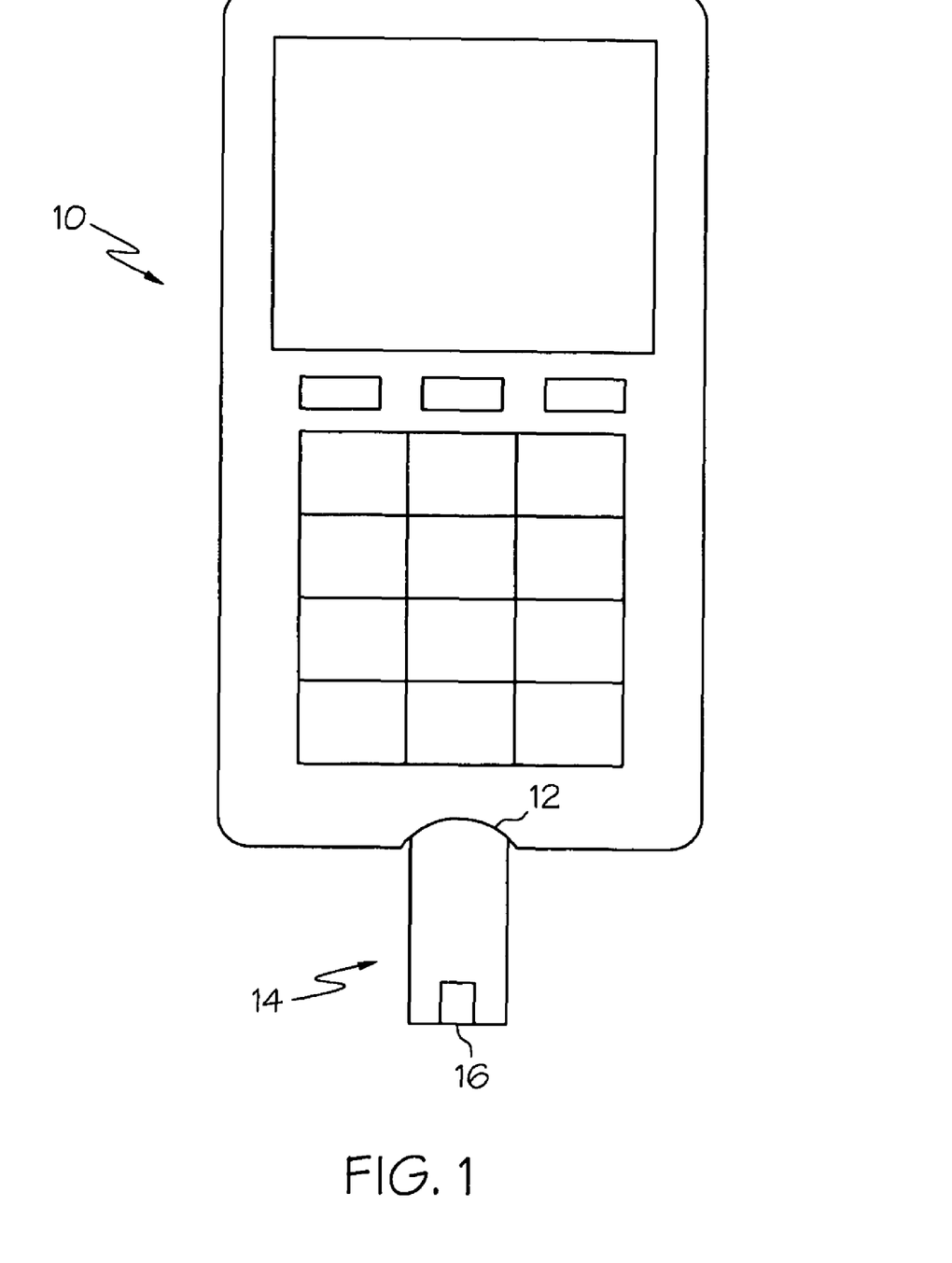
FIG. 1 depicts an exemplary portable electronic device capable of blood glucose measurement according to one or more embodiments shown and described herein.

Referring to FIG. 1, an exemplary bG measuring device 10 configured as a cellular phone is illustrated. It will be understood that the bG measuring device may be configured as other types of portable electronic device, such as music players, personal digital assistants, smart phones, insulin pumps and others. The bG measuring device 10 comprises a measurement strip port 12 that may be operable to receive a measurement strip 14, which may be removably inserted into the measurement strip port 12. The measurement strip port 12 may be integrated into the housing of the cellular phone. The geometry of the port 12 may provide enough chamfer and guiding surfaces to ease the insertion of the measurement strip 14 into the port 12. It will be understood that other embodiments of the slot and the strip port are also possible. The measurement strip 14 may be configured to receive a blood sample in the form of a blood drop at a reaction site 16 located at a point along the measurement strip 12, such as near the tip. The measurement strip 14 may contain electronic circuitry and/or chemicals at the reaction site 16 which facilitate the measurement of the bG level of a blood sample.

Figure 2A:
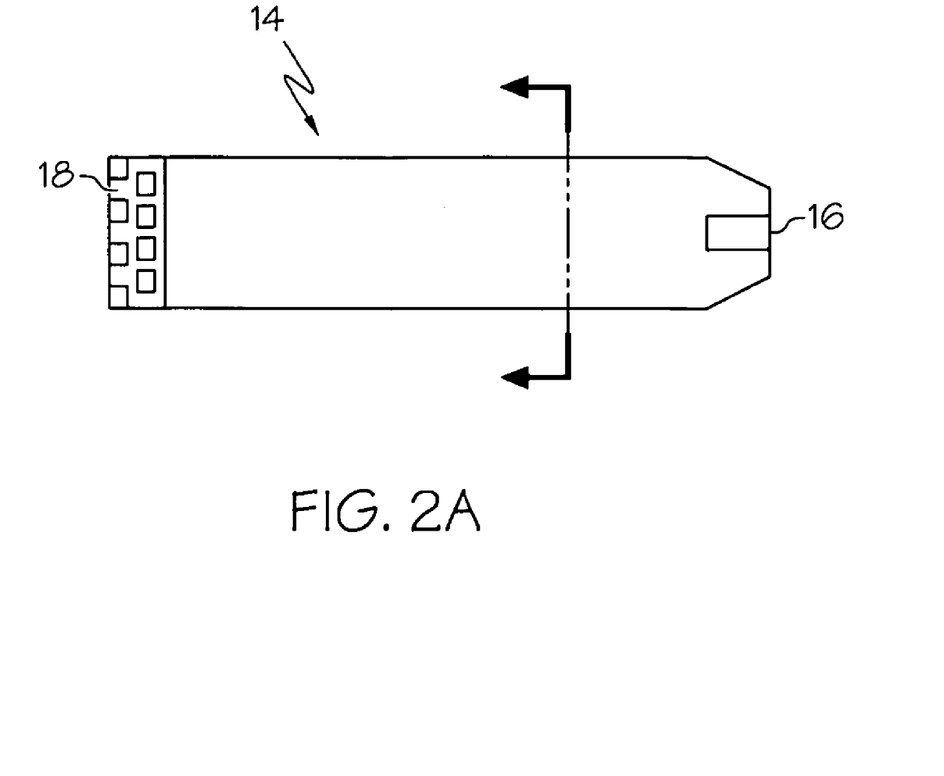
FIG. 2A depicts an exemplary measurement strip according to one or more embodiments shown and described herein.
Figure 2B:
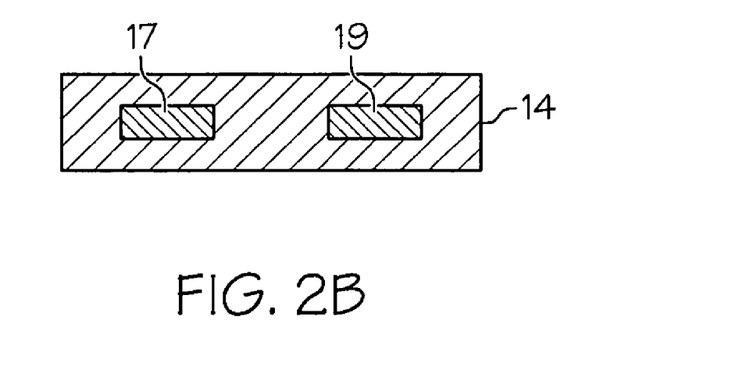
FIG. 2B depicts a cross section view of the exemplary measurement strip depicted in FIG. 2A according to one or more embodiments shown and described herein.

Referring to FIGS. 1, 2A and 2B, the measurement strip port 12 may have a plurality of electrical pads (not shown) which are configured to engage corresponding electrical pads 18 at the base of the measurement strip 14 when installed in the measurement strip port 12. In one embodiment, the measurement strip port 12 and measurement strip 14 may have six electrical pads 18. In another embodiment, the strip port and strip may have eight electrical pads 18. Electrodes 17 and 19, which may be made of a metal material such as gold or palladium, may traverse the measurement strip 14 from the reaction site 16 to the base and electrical pads 18. The electrodes electrically couple the reaction site 16 to the electrical pads 18 and measurement strip port 12.

Figure 3:
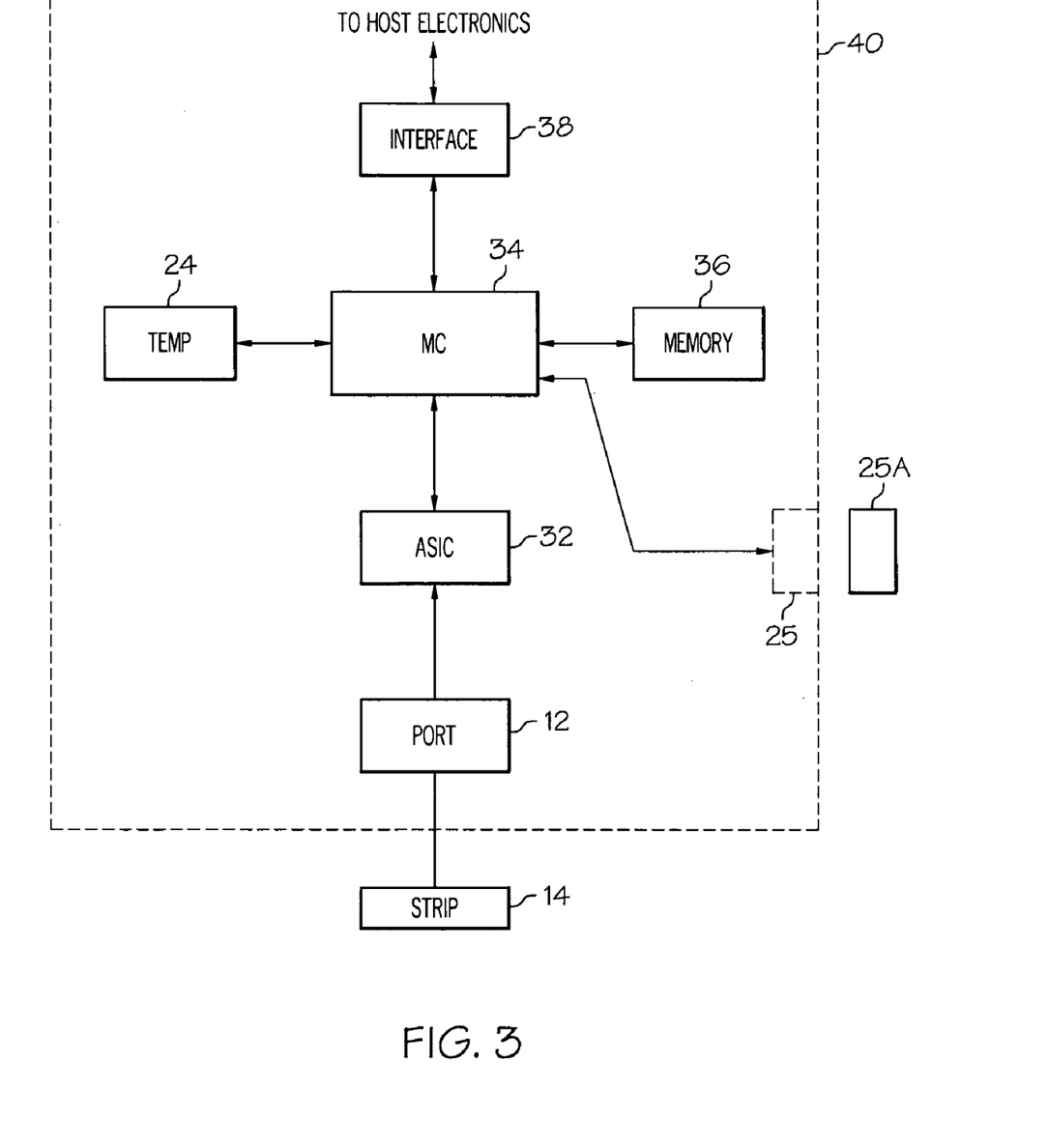
FIG. 3 depicts a schematic of a blood glucose measuring module according to one or more embodiments shown and described herein.

FIG. 3 is a schematic of exemplary bG measuring circuitry 40 of a portable electronic device that is capable of measuring blood glucose, such as the cellular phone illustrated in FIG. 1. It will be understood that the exemplary bG measuring circuitry 40 is only one configuration as other hardware and software configurations may be utilized to effectuate the temperature estimation and dynamic thermal models described herein. The bG measuring circuitry 40 of the embodiment illustrated in FIG. 3 comprises an interface 38, a bG microcontroller 34, an application specific integrated circuit ("ASIC") 32, a measurement strip port 12, a temperature measurement element 24 and memory 36. The bG measuring circuitry 40 may also comprise a code key port 25 in which to receive a code key 25A containing calibration information. The bG measuring circuitry 40 may be integral with other dedicated circuitry of the portable electronic device, or the bG measuring circuitry 40 may be configured as an embeddable bG module that may be installed in an external host having a host processor as disclosed in copending and commonly owned U.S. patent application Ser. No. 12/477,982, the entirety of which is hereby incorporated by reference herein. For example, when installed in an external host having a host processor, an embeddable bG module comprising the bG measuring circuitry 40 may be used as an embedded measurement engine for a glucose measurement system within the external host.

Referring still to FIG. 3, the bG microcontroller 34 may be in electrical communication with the interface 38, the ASIC 32, and the temperature measuring element 24. The bG microcontroller 34 may be in electrical communication with other circuit modules of the portable electronics device ("non-bG modules") in which the bG measuring circuitry 40 is implemented. As described below, the interface 38 may enable the bG microcontroller 34 to communicate with a cellular phone microcontroller (not shown), for example, to determine particular attributes of components operating within the cellular phone. In some embodiments, the interface 38 may be incorporated directly into the bG microcontroller 34 such that there is no dedicated interface 38 circuitry and the bG microcontroller 34 may communicate directly with other non-bg modules within the portable electronics device.

In one embodiment, the bG microcontroller 34 may be model MSP430CG4619, manufactured by Texas Instruments, Inc. Other types and sizes of microcontrollers from Texas Instruments as well as other manufacturers may also be used. In this embodiment, the bG microcontroller 34 may contain a Universal Asynchronous Receiver Transmitter (UART), timers, programmable input/output (I/O) pins, data memory, program memory, and other functions which may facilitate its operation. The bG microcontroller 34 may execute a computer program, hereinafter called "bG measurement software," which defines and/or enables the functioning of the bG measurement circuitry 40. The bG measurement software may be written in a computer language, such as "C" or assembly language, and may be stored in the program memory of the bG microcontroller 34.

The ASIC 32 may be in electrical communication with the bG microcontroller 34 as well as the measurement strip port 12. The ASIC 32 may be a mixed-signal device, having both digital and analog components. When a measurement strip 14 is inserted into the measurement strip port 12, the ASIC 32 may be operable to electrically detect the insertion and, subsequently, communicate with the measurement strip port 12 such that the ASIC 32 may receive signals from the measurement strip 14 related to the blood glucose level of a blood sample placed on the reaction site 16. The ASIC 32 may, after receiving the signals from the measurement strip 14, process these signals and communicate information about the bG level to the bG microcontroller 34. The bG microcontroller 34, in turn, may take this information and process it further in order to arrive at the final bG measurement result. Thus, the ASIC 32 and the bG microcontroller 34 may work together to perform the bG measurement function, with the ASIC 32 performing part of the function and the bG microcontroller 34 performing part of the function. The ASIC 32 may be housed in an electrical ball-grid array (BGA) package or other suitable package. The ASIC 32 may additionally perform other functions such as generating a fixed-frequency clock signal for the bG microcontroller 34. The ASIC 32 and bG microcontroller 34 may communicate with each other via a serial bus, such as I$^2$C or SPI, or via a parallel interface.

Referring still to FIG. 3, the bG measuring circuitry 40 may also include a non-volatile configuration memory 36. This memory may be external to the bG microcontroller 34, as is depicted in FIG. 3, or may be integrated into the bG microcontroller 34. The memory 36 may be operable to store information relating to the operation of the module, such as configuration parameters, calibration data for the measurement strips, and so forth. Further, the memory may be operable to store the dynamic thermal model and the impulse response matrix for each heat generating component, as describe in detail below. The memory 36 may in electrical communication with the bG microcontroller 34 such that the data stored in the memory may be read by the bG microcontroller 34. In addition, the bG microcontroller 34 may write data to the memory 36 such that the data is stored on the memory 36 in a non-volatile fashion. The memory 36, when it is external to the microcontroller, may be a 64 kilobit device, such as a 25AA640A device from Microchip Technology, Inc. Other types of memory, including flash memory, may also be utilized.

The interface 38 may employ a serial communication scheme to provide communication between the bG microcontroller 34 and non-bg module(s) of the portable electronics device. The serial data interface may employ a "hard-wired" scheme, such a UART or Universal Serial Bus (USB). In this embodiment, the communication signals between the bG measuring circuitry 40 and the non-bg modules may be implemented with electrical conductors. Furthermore, the connection may be made through an electrical connector. The UART may employ two signals: One signal may transmit data from the non-bg module to the bG measuring circuitry 40, and the other signal may transmit data from the bG measuring circuitry 40 to the non-bg module. Other communications schemes, such as parallel or infrared communication, may also be utilized.

The embeddable module 10 may also include a code key port 25. The code key port 25 may allow the user to install an external code key 25A which may contain calibration information related to the measurement site 16. This calibration information may permit the bG measuring circuitry 40 to improve the accuracy of the bG measurement due to, for example, slight variations in the measurement strip which may have been introduced during the manufacturing process. Thus, in order to improve the accuracy of the bG measurement, the measurement strip 14 (or, typically, package of strips) may also include a code key 25A which is operable to store information relating to calibration data for the strip 14 (or package of strips). When inserted into the code key port 25, the calibration information contained on the code key 25A may be read by the bG microcontroller 34. As a result, when a bG measurement is performed, the code key 25A may provide calibration information which permits the bG microcontroller 34 to improve the accuracy of the bG measurement.

Referring still to FIG. 3, the temperature measuring element 24 may be used to measure the internal temperature of the bG measuring device 10 and to estimate the temperature of the measurement strip 12. The temperature measuring element 24 may be in electrical communication with the bG microcontroller 34 such that the bG microcontroller 34 may request a temperature measurement during a bG measurement session or any other time. In one embodiment, the temperature measuring element 24 may comprise a thermistor, the resistance of which is a known function of temperature. Other embodiments may use similar devices, such as semiconductor temperature sensors, resistance thermal devices (RTDs) and thermocouples. The temperature measurement may be used to improve the accuracy of the bG measurement. As discussed in detail below, the temperature measurement provided by the temperature measuring element 24 may also indicate conditions in which the bG measurement should not be made, such as when the ambient temperature in which the bG measuring device 10 is operating is outside of the operating range of the measurement strip 14. For example, a measurement strip 14 may be designed to operate from 10 degrees C. to 40 degrees C. Outside this range, the measurement strip 14 may not produce sufficiently accurate results. Thus, when the ambient temperature falls outside this range, the bG measuring circuitry 40 may recognize this condition and may refuse to take a measurement under such conditions, since the result may not be sufficiently accurate.

Although the primary components of the bG measuring circuitry 40 have been described (e.g., the microcontroller, the ASIC, etc.), the bG measuring circuitry 40 may comprise additional components, such as but not limited to resistors, capacitors, inductors, transformers, transistors, and diodes. These additional components may be used to facilitate the operation of the bG measuring device 10. For example, one or more capacitors may be electrically connected to the power supply voltage in order to provide filtering for the bG measuring circuitry 40. As another example, inductors may be placed between the bG microcontroller 34 and the measurement strip port 12 so as to reduce the possibility of damage to the bG microcontroller 37 due to an electrostatic discharge generated by the user when inserting the measurement strip 14 into the measurement strip port 12. Additional electronic components may be used to perform similar functions.

Dynamic thermal models providing estimations of the temperature at a bG measurement strip reaction site 16 when the reaction site 16 may be at a different temperature than the internal temperature of the bG measuring device 10 will now be described. As discussed above, it may be important to know the temperature at the measurement strip reaction site 16 in order to avoid unwarranted under or over-temperature lockout conditions that would prevent proper use of the bG measuring device 10. Referring to FIG. 1, in some embodiments, all but the base of the measurement strip 14 is exposed to the ambient air. It may be shown that the reaction site temperature is governed primarily by convective heat exchange with the ambient air and that the thermal conductivity of the strip is so low that the temperature of the inserted end of the measurement strip 14, which is close to the internal temperature of the bG measuring device 10, will have little measurable effect on the temperature at the other end of the strip 14 wherein the reaction site 16 is located. Therefore, the reaction site temperature closely follows the ambient air temperature.

Embodiments described herein utilize a dynamic thermal model that uses a temperature sensor reading to dynamically estimate the reaction site temperature depending on how the portable electronic device is being used. As described in detail herein, embodiments utilize linear superposition of temperature elevation responses of a particular heat generating component over time to determine a total temperature elevation of the particular heat generating component based on the activity characteristics of each heat generating component. From this total temperature elevation and an internal temperature provided by the temperature measuring element 24, an estimation of the temperature of the reaction site 16 on the measurement strip 14 may be achieved.

Figure 4:
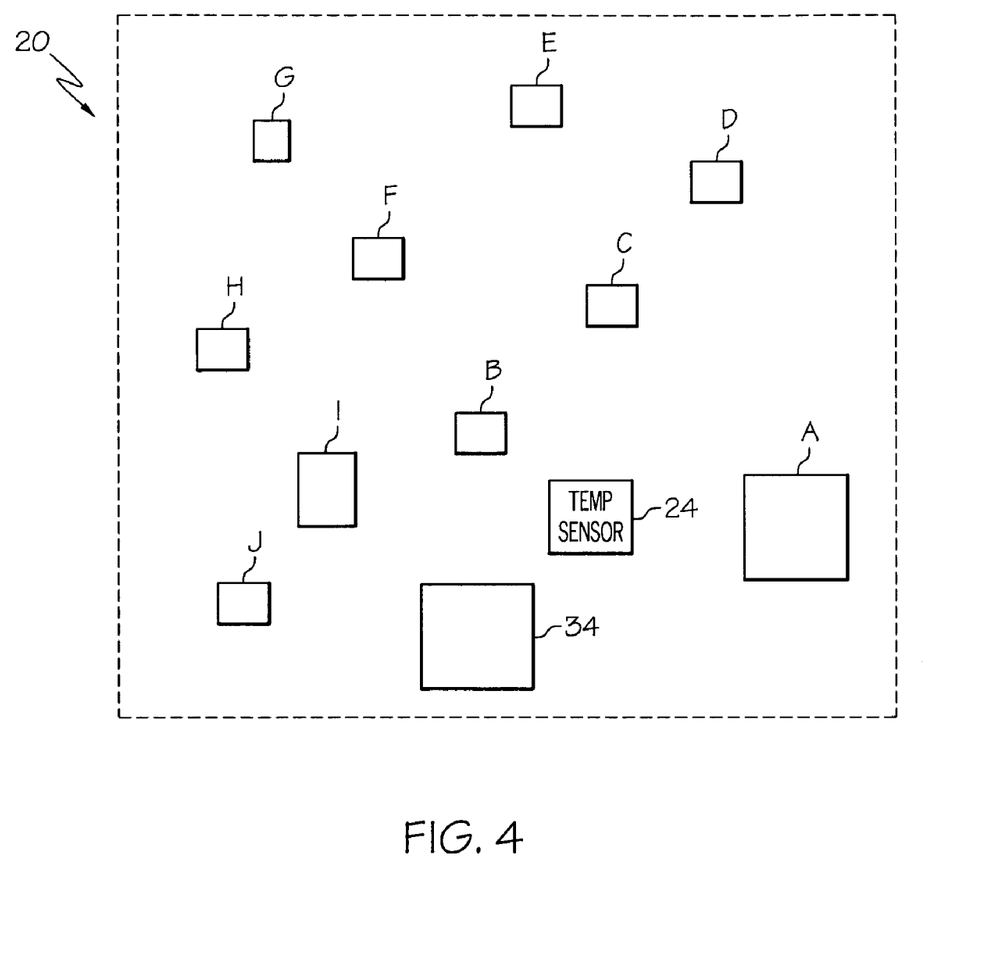
FIG. 4 depicts a portion of a printed circuit board of a portable electronic device having a blood glucose measurement module.

Now referring to FIG. 4, a schematic of an exemplary bG measuring device printed circuit board ("PCB") 20 is illustrated. The PCB 20, which may comprise several layers of copper and has a plurality of electronic components, including the bG microcontroller 34 and temperature sensor 24. FIG. 4 is for illustrative purposes only and embodiments of the present disclosure are in no way limited thereto. It will be understood that additional PCBs may be located within the bG measuring device 10. Located on the PCB are a plurality of heat generating components A-J. The heat generating components, may be any electrical component that generates heat, such as microcontrollers, radio frequency power amplifiers, audio amplifiers, batteries, voltage regulators, and the like. For example, heat generating component A may be a communications microcontroller in a cellular phone application, while heat generating component F may be a resistor. The bG microcontroller 34 may also generate heat.

A number of factors may affect the temperature response of a given heat source at the temperature measuring element 24. Within the device 10 enclosure, the heat source may be located on the same circuit board as the temperature measuring element 24 or on another circuit board, and it may be near the sensor or far from it. The heat generation of a particular electronic component may vary greatly during its various modes of operation. The corresponding temperature response at the temperature measuring element 24 may be measured with reasonable accuracy. Depending on the location of the heat producing electronic component relative to the temperature measuring element 24 and the nature of the thermal pathways between them (e.g., the thermal resistance of the PCB substrate or substrates), the temperature response at the temperature measuring element 24 may vary a great deal from component to component. A heat generating component near the temperature measuring element 24 (e.g., heat generating component B) may tend to produce a rapid rise in temperature as measured by the temperature measuring element 24 after the heat is applied, followed by a rapid decline in temperature when the heat is removed. For a more distant heat generating component (e.g., heat generating component G), the rise and fall in temperature may be more gradual and more time may elapse before the peak temperature is reached.

Despite a temperature measuring element 24 that may be providing a signal to the bG microcontroller 34 that is changing at a rate that exceeds a specified threshold, embodiments of the present disclosure may obtain an improved estimate of the ambient air temperature, and hence the reaction site 16 temperature, by amplifying those changes in the temperature measuring element 24 reading and formulating a new prediction based on a dynamic thermal model of the bG measuring device 10. As described above, difficulties may arise when the reading from the temperature measuring element 24 is changing not due to changes in the ambient air, but rather due to the internal heating of electronic components inside the device containing the bG circuitry.

Using the cellular phone embodiment illustrated in FIG. 1 as an example, due to the high operating temperature of circuitry inside of a cell phone 10, the temperature readings from the temperature measuring element 24 may be unduly elevated. The internal heat caused by the heat generating components A-J may vary depending on how the cell phone 10 is being used. For example, a recent and lengthy talk session may cause a significant rise in internal temperature that should be accounted for. Similarly, the heat generated by a lengthy talk session that occurred forty-five minutes prior to the bG measurement test may have dissipated. Accurate temperature estimation should continue even when the thermal characteristics of the device change with specific usage.

Embodiments of the present disclosure utilize a dynamic thermal model that provide for estimating the temperature elevation due to any number of heat sources of arbitrary strength and arbitrary duration in a bG measuring device. Once the total expected temperature elevation has been determined from the dynamic thermal model, then this quantity may be subtracted from the temperature reading of the temperature measuring element 24 to furnish a corrected temperature reading upon which an accurate ambient temperature prediction may be based. The thermal model may be dynamically adjusted depending on the specific usage of the device. As more functions are added to the meter, (e.g., communication capabilities, multimedia capabilities, etc.) it becomes increasingly important to estimate reaction site 16 temperature based on how the device 10 has been used prior to the bG measurement test.

Figure 5:
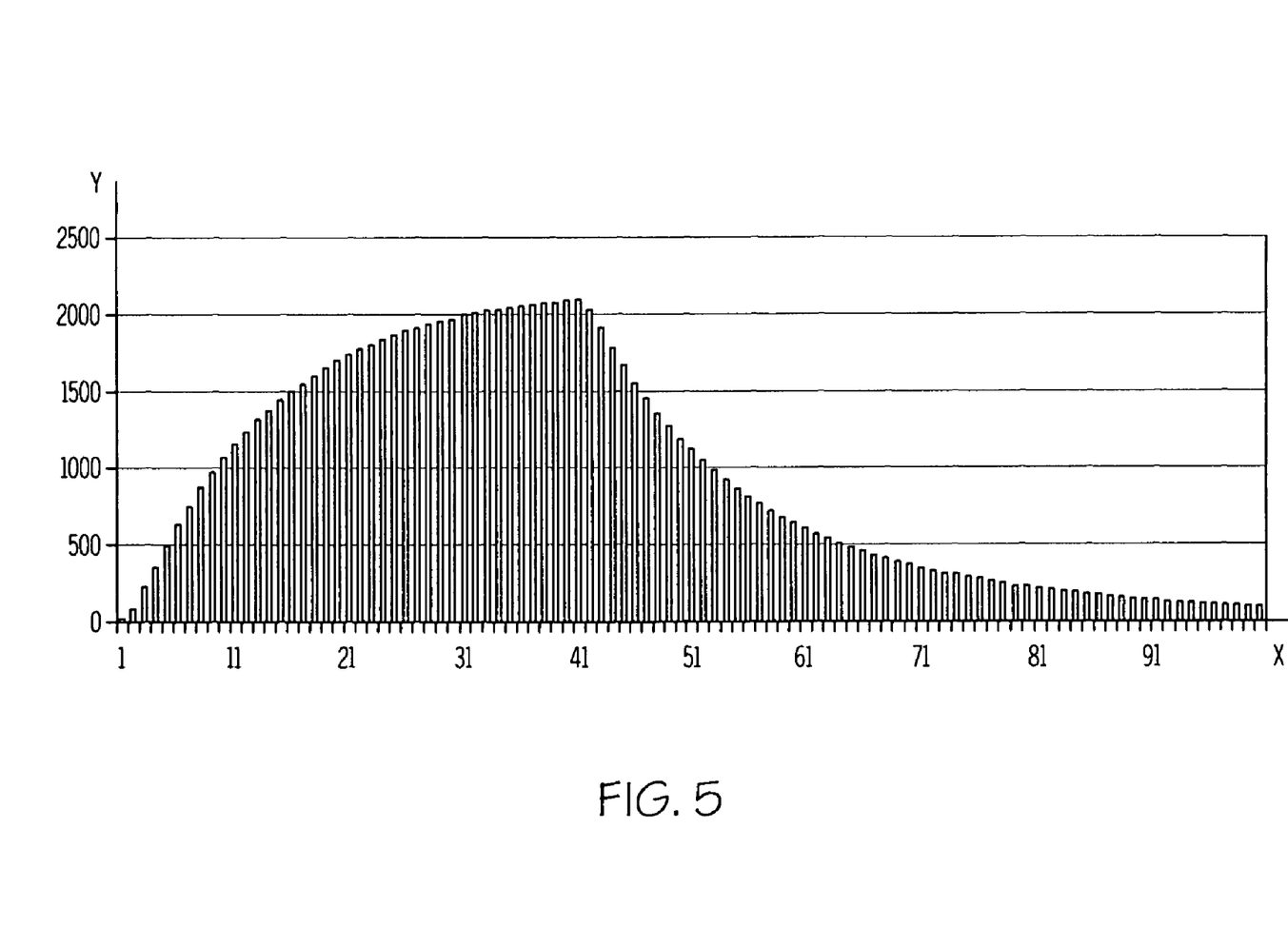
FIG. 5 depicts a succession of impulse responses of a heat generating component within a device that is generating heat at a particular magnitude for forty minutes followed by a period of sixty minutes in which the heat generating component is not generation heat.

Dynamic thermal models of the present disclosure rely upon the linear superposition of temperature responses to an applied heat generating component or components. A time-varying heat source may be characterized as a series of heat "impulses" of varying magnitude. An "impulse" may be defined as period of heating lasting a short time as compared to the total duration of heating. Due to linear superposition, the temperature response of a heat generating component of extended duration can be found by adding up the temperature responses of a succession of impulses that represent that heat generating component. FIG. 5 is a graph illustrating a succession of impulse responses of a heat generating component within a device that is generating heat at a particular magnitude for forty minutes followed by a period of sixty minutes in which the heat generating component is not generating heat. The x-axis is time in minutes and the y-axis is in hundredths of a Fahrenheit degree. The information illustrated in graph may be utilized to determine the temperature elevation of a particular heat generating element at a particular time.

Within a bG measuring device there may be multiple sources of heat. Again by linear superposition, the total temperature response of all of these heat generating components may be found by summing their individual contributions. These heat sources may become active prior to or during a blood glucose measurement. The dynamic thermal model may be used to characterize the combined effect of multiple, time-varying heat sources in a portable electronic device incorporating bG measurement circuitry. Referring to FIG. 4, consider the case of a heat generating component "A" of strength Qa being applied for duration (Na/2)·Δt, where Na is an even positive integer and Δt is an increment of time. The temperature measuring element 24 is installed in the bG measuring device 10 at a location different than the heat source. The temperature elevation at the location of the temperature sensor at time ti=i·Δt after the activation of the heat source may be described by:

$$Ea_i = (Ta_i - T_{ref}) \qquad \text{Eq. (1)}$$

where $Ta_i$ is the temperature at the location of the temperature sensor at time $t_i$ and $T_{ref}$ is a suitable reference temperature. The reference temperature may $T_{ref}$ be the ambient temperature of the bG measuring device 10 such that $T_{ref} = T_{amb}$.

Using equation (1), the temperature elevations $Ea_i$ for times $t_1$ through $t_{Na}$ may therefore be expressed by the following matrix equation:

$$Qa \cdot \begin{bmatrix} 1 & 0 & \cdots & & 0 & 0 & \cdots & & 0 \\ 1 & 1 & 0 & \cdots & 0 & 0 & \cdots & & 0 \\ 1 & 1 & 1 & 0 & \cdots & 0 & 0 & \cdots & & 0 \\ \cdots & & & & & \cdots & & & \\ 1 & \cdots & & 1 & 0 & 0 & \cdots & & 0 \\ 1 & 1 & \cdots & 1 & 1 & 0 & \cdots & & 0 \\ 0 & 1 & \cdots & & 1 & 1 & 0 & \cdots & 0 \\ 0 & 0 & 1 & \cdots & & 1 & 1 & 0 & \cdots & 0 \\ 0 & 0 & 0 & 1 & \cdots & 1 & 1 & 1 & \cdots & 0 \\ \cdots & & & & & \cdots & & & \\ 0 & \cdots & & 0 & 1 & 1 & \cdots & & 1 & 0 \\ 0 & 0 & \cdots & & 0 & 1 & 1 & \cdots & & 1 \end{bmatrix} \qquad \text{Eq. (2)}.$$

$$\begin{bmatrix} A_1 \\ A_2 \\ \vdots \\ A_{Na} \end{bmatrix} = \begin{bmatrix} Ea_1 \\ Ea_2 \\ \vdots \\ E_{Na} \end{bmatrix},$$

Or, the matrix equation may be more simply expressed as:

$$Qa \cdot [U] \cdot [A] = [Ea], \qquad \text{Eq. (3)}$$

where:

Qa is the magnitude of the heat generating component at location "A;"

[U] is a matrix of unit impulses;

[A] is a matrix of impulse responses; and

[Ea] is a matrix of temperature elevations.

If the magnitude Qa of the heat source and the temperature elevations from times $t_1$ through $t_{Na}$ are known, then the impulse responses $[A_i]$, i=1 to Na, may be determined.

Likewise for a heat generating component at point "B" of strength Qb applied for duration (Nb/2)·Δt, the temperature elevations $Eb_i$ for times $t_1$ through $t_{Nb}$ may be expressed by the following matrix equation:

$$Qb \cdot [U] \cdot [B] = [Eb], \qquad \text{Eq. (4)}$$

where:

Qb is the magnitude of the heat generating component at point "B;"

[U] is a matrix of unit impulses;

[B] is a matrix of impulse responses; and

[Eb] is a matrix of temperature elevations.

Similarly, if the magnitude Qb of the heat sources and the temperature elevations from times $t_1$ through $t_{Nb}$ are known, then the impulse responses $[B_i]$, i=1 to Nb, may be found.

In order to characterize any given heat generating "X" among those being considered, the total time duration Nx·Δt should be sufficiently long that for time t>Nx·Δt, the magnitude of the impulse response is approximately zero, i.e., $X_i \approx 0$ for i>Nx. Let Nx be an even number chosen such that either $X_{Nx-1} > 0$ and $X_i = 0$ for i>Nx−1; or $X_{Nx} > 0$ and $X_i = 0$ for i>Nx. In other words, $X_i$ is truncated to zero for i>Nx. The interval Δt corresponds to the "impulse" interval, a suitably short interval of time over which a heat generating component of a unit strength acts. The interval Δt should be small compared to the total duration Nx·Δt over which the temperature elevations resulting from the applied heat generating component persist in the enclosure of the electronic device.

For all heat generating components of interest, let N be a number equal to the maximum of the individual interval counts Na, Nb, etc.:

$$N \geq \max\{Na, Nb, \ldots\}$$

Hence for any given heat generating component, the impulse response at time $t_i$ where $i \leq N$ may be zero:

$A_i \geq 0$ for $1 \leq i \leq Na, A_i = 0$ for $i > Na$, and $Na \leq N$;

$B_i \geq 0$ for $1 \leq i \leq Nb, B_i = 0$ for $i > Nb$, and $Nb \leq N$; and etc. for all heat sources Thus chosen, the upper limit N on the interval counts will be sufficiently large that the matrix of impulse responses for each and every heat source may be characterized with minimal loss due to truncation.

The maximum period of time that the temperature response due to an input of heat from any of the components is tracked is given by $N \cdot \Delta t$, where N is the total number of samples and $\Delta t$ is the sampling interval. From the standpoint of the dynamic thermal model, N is the total number of elements in the impulse temperature response matrix [X] (dimension $N \times 1$) and $\Delta t$ is the impulse duration. For a handheld electronic device, this maximum period may be on the order of one to two hours. By that time, virtually all of any generated heat will have been dissipated to the environment of the device. The sampling interval $\Delta t$, which is also the assumed impulse duration, should be small enough to resolve the time-varying temperature response from a transient heat release with a sufficient degree of precision that reasonably accurate estimates of the individual and total temperature elevations can be calculated.

For a handheld electronic device, a suitable sampling interval might be on the order of several seconds to a few minutes. The exact choice depends on the nature of the heat generating components and the degree of precision desired. A sampling interval of one minute may provide adequate results for particular handheld devices. For a maximum tracking period of one hour, a one minute sampling period would yield N=60 samples, and hence 60 elements in the impulse temperature response matrices for the various components. As a further refinement of the method and described in more detail below, if the heat being released by a particular heat generating component varies during a given sampling period, then the reported strength of that source (which is known by the electronic control) may be adjusted to give a representative average over the interval.

In order to develop the impulse response matrix (e.g., [A], [B], etc.) of each of the various heat generating components in a bG measuring device, a series of simple experiments may be performed. For each heat generating component "X" (e.g., "A", "B", etc.), the following procedure may be followed:

1) Allow the bG measuring device to come to equilibrium temperature with its environment. The ambient temperature is the reference temperature:

$T_{ref} = T_{amb}$

2) Activate heat source "X" at constant strength Qx for a duration of $(N/2) \cdot \Delta t$, where N and $\Delta t$ have been chosen in the manner described above (i.e., $N \geq \max\{Na, Nb, \ldots\}$ and $\Delta t$ is a suitable impulse interval). Record the initial temperature at the temperature sensor at the time that the heat source is activated and the temperature at each succeeding time $t_i = i \cdot \Delta t$, $i = 1$ to $N/2$.

3) At time $t = (N/2) \cdot \Delta t$, deactivate the heat generating component "X" and continue recording the sensor temperature at times $t_i = i \cdot \Delta t$, $i = (N/2) + 1$ to N.

4) Calculate the temperature elevation at each time step:

$Ex_i = (Tx_i - T_{ref}), 0 \leq i \leq N,$ Eq. (5)

5) Using matrix methods, determine the matrix of impulse temperature responses, [X]:

$Qx \cdot [U] \cdot [X] = [Ex],$ Eq. (6)

$[X] = (1/Qx) \cdot [U]^{-1} \cdot [Ex],$ Eq. (7)

6) Repeat the above steps for each heat generating component of interest.

During the course of the above procedure, the ambient environment of the bG measuring device 10 should be held to conditions representative of the environment in which the device is expected to be used. For example, if the device will spend most of its time in still air at room temperature, then these conditions should be maintained during the experiments. If the operating environment is expected to be drafty, then a suitable airflow should be imposed. It will be understood that the impulse response matrices may be developed by procedures other than the procedure described above. For example, the impulse response matrices may be developed by computer simulations and not actual experimentation and measurement.

The above discussion considered heat generating components operating at a constant magnitude Qx. Consider now a sequence of heat impulses from heat generating component "K" having duration $\Delta t$ and variable magnitude [Qk] beginning at time $N \cdot \Delta t$ prior to the present:

$[Qk] = [Q_{k,1} \, Q_{k,2} \ldots Q_{k,N-1} \, Q_{k,N}],$ Eq. (8)

where the magnitudes of the heat impulses may be given by:
Qk,1 is the magnitude at time $t = -N \cdot \Delta t$
Qk,2 is the magnitude at time $t = -(N-1) \cdot \Delta t$
Qk,N-1 is the magnitude at time $t = -2 \cdot \Delta t$
Qk,N is the magnitude at time $t = -1 \cdot \Delta t$.

Therefore, the magnitude of heat generated by component K varies over time. For example, a particular component, such as an audio amplifier used in a communications circuit of a cellular phone may operate at a different temperature at varying points during a phone call. Similarly, a current of varying amplitude may pass through a resistor during a call. The temperature elevation Ek due to this sequence of heat impulses from heat generating component K may be given by:

$$E_k = \sum_{i=1}^{N} Q_{k,i} \cdot X_{k,N-i+1},$$ Eq. (9)

or:

$$E_k = \sum_{i=1}^{N} Q_{k,N-i+1} \cdot X_{k,i},$$ Eq. (10).

where $[X_k] = [X_{k,1} \, X_{k,2} \ldots X_{k,N-1} \, X_{k,N}]$ is the impulse temperature response for heat generating component K. According to equations (9) and (10), the temperature elevation $E_k$ due to heat generating component K at time i may be found by summing the impulse responses due to the variable magnitude Qk prior to time i.

Once the impulse response matrices for all of the heat sources have been determined, whether the magnitude of the heat generating component Q is constant or variable, then the principle of superposition may be applied to determine the expected temperature response of the device to the influence of any combination of heat generating components acting at arbitrary strengths and for arbitrary durations. For example, the total temperature elevation due to M sources may be expressed as:

$$E_{total} = \sum_{k=1}^{M} E_k = \sum_{k=1}^{M}\sum_{i=1}^{N} Q_{k,N-i+1} \cdot X_{k,i},\qquad \text{Eq. (11)}.$$

Note that the effect of any temperature impulse prior to time $-N \cdot \Delta t$ is considered negligible and therefore no corresponding source terms are included in the calculations. This total temperature elevation $E_{total}$ due to the internal heat generating components of the bG measuring device may now be subtracted from the temperature sensor reading to yield a corrected reaction site temperature $T_{site}$:

$$T_{site} = T_{sensor} - E_{total},\qquad \text{Eq. (12)}.$$

In this manner, a prediction of the ambient temperature and, hence, the effective test strip reaction site temperature, may be obtained despite the changing internal temperature signal provided by the heat measuring element 24.

The bG microcontroller 34 should know which heat generating components are being activated, and at what strength and for how long. This information plus the reading of the temperature measuring device 24 mounted on the PCB of the bG measurement circuitry 40 may be used to determine the temperature response to heat released by each of the heat generating components. In operation, the impulse response matrix for each heat generating component of interest may be stored in the non-volatile memory 36 or within the microcontroller 34. The bG microcontroller 34 is operable to read a temperature signal from the temperature measuring element 24. At the time of a bG measurement test, or any other time, the bG microcontroller 34 is operable to communicate with the other non-bG modules either via the interface 38 or directly to obtain activity characteristic information regarding the heat generating components of interest. The activity characteristic information may include the initiation time that a heat generating component became active, the duration in which the heat generating component had been active and the magnitude at which the heat generating component had been active.

The various controllers of the non-bG modules may provide the activity characteristic information to the bG microcontroller 34. Using the cellular phone embodiment of FIG. 1 as an example, the cellular phone microcontroller may transmit the activation initiation time, activation duration time and thermal magnitudes of each heat generating component when requested by the bG microcontroller. In another embodiment, the cellular phone microcontroller may provide a code to the bG microcontroller that indicates when a cellular phone call was initiated and when or if the call was ended. With this information, the bG microcontroller may have stored within its memory (or within the non-volatile memory 22) thermal magnitude and durational information for the particular heat generating components.

At the time of a bG measurement test, the bG microcontroller 34 may obtain the activity characteristics for each heat generating component of interest from the non-bG modules and the internal temperature provided by the temperature measuring element 24. With this information, the bG microcontroller 34 may initiate the dynamic thermal model by retrieving the impulse response matrix for each heat generating component of interest. Based on the timing and type of function initiated by the bG measuring device (e.g., a phone call), the bG microcontroller 34 may calculate the temperature elevations Ex for each heat generating component of interest utilizing the superposition method as described above (e.g., Eqs. 3 and 4). The bG microcontroller 34 may then determine a total temperature elevation $E_{total}$ due to the heat generating component by superposition and subtract that total from the temperature value $T_{sensor}$ provided by the temperature measuring device 24 to achieve a reaction site temperature estimate $T_{site}$. The bG microcontroller 34 may then take appropriate action based on the reaction site temperature estimate $T_{site}$ such as preventing a measurement test if $T_{site}$ is not within certain bounds, or allowing measurement test if $T_{site}$ is within the bounds.

It should now be understood that blood glucose measuring devices described herein may be operable to provide a temperature estimation of a reaction site on a blood glucose measuring strip. The dynamic thermal model of the disclosed embodiments may predict the reaction site temperature despite any changing internal device temperatures measured by an internal temperature measuring element.

For the purposes of describing and defining embodiments of the present disclosure it is noted that the term "approximately" is utilized to represent the inherent degree of uncertainty that may be attributed to any quantitative comparison, value, measurement, or other representation.

It is noted that recitations herein of a component of a particular embodiment being "programmed" in a particular way, "configured," "programmed" or "operable" to embody a particular property, or function in a particular manner, are structural recitations as opposed to recitations of intended use. More specifically, the references herein to the manner in which a component is "programmed," "configured" or "operable" denotes an existing physical condition of the component and, as such, is to be taken as a definite recitation of the structural characteristics of the component.

Having described the invention in detail and by reference to specific embodiments thereof, it will be apparent that modifications and variations are possible without departing from the scope of the invention defined in the appended claims. More specifically, although some aspects of the present invention may be identified herein as preferred or particularly advantageous, it is contemplated that the present invention is not necessarily limited to these preferred aspects of the invention.

What is claimed is:

1. A method of estimating the temperature of a reaction site on a measurement strip in a blood glucose measuring device having a plurality of heat generating components and a temperature measuring element, the method comprising:

determining, by a microcontroller, an activation initiation time, when a heat generating element becomes active, an activation duration time, how long a heat generating element had been active within a sample period, and a thermal magnitude Qx at which a heat generating element had been active within the sample period for each of the heat generating components;

determining, by a microcontroller, a temperature elevation Ex for each of the heat generating components, wherein the temperature elevation Ex for each of the heat generating components is determined at least in part by an impulse response matrix $[X_i]$ for times $t_1$ through $t_{Nx}$, the activation initiation time, the activation duration time and the thermal magnitude Qx for each of the heat generating components;

determining, by a microcontroller, a total temperature elevation $E_{total}$ of the glucose measuring device by summing the temperature elevation Ex of each of the heat generating components;

reading, by a microcontroller, a temperature value $T_{sensor}$ provided by the temperature measuring element; and determining, by a microcontroller, a reaction site temperature estimation $T_{site}$ by subtracting the total temperature elevation $E_{total}$ from the temperature value $T_{sensor}$ provided by the temperature measuring element.

2. The method as claimed in claim 1 further comprising preventing a blood glucose test if the reaction site temperature estimation $T_{site}$ is greater than a maximum reaction site temperature $T_{max}$ or less than a minimum reaction site temperature $T_{min}$.

3. The method as claimed in claim 1 wherein the impulse response matrix $[X_i]$ for each heat generating component comprises a plurality of impulse response values $X_i$ and the act of determining the temperature elevation Ex for each of the heat generating components further comprises summing the impulse response values $X_i$ corresponding to the activation initiation time, the activation duration time and the thermal magnitude Qx of each heat generating component.

4. The method as claimed in claim 1 wherein determining the temperature elevation Ex for each of the heat generating components is described by:

$$[Ex_i] = Qx \cdot [U] \cdot [X_i];$$

where:
- $[Ex_i]$ is a temperature elevation matrix of a heat generating component;
- Qx is the thermal magnitude of a heat generating component;
- [U] is a unit impulse matrix; and
- $[X_i]$ is the impulse response matrix of a heat generating component.

5. The method as claimed in claim 4 wherein:
the method further comprises determining a temperature elevation $E_k$ for a heat generating component k having a sequence of heat impulses of duration $\Delta t$ and a variable magnitude $[Q_k]$ beginning at a time $N \cdot \Delta t$ such that $$E_k = \sum_{i=1}^{N} Q_{k,N-i+1} \cdot X_{k,i}$$

where N is the total number of values in the impulse response matrix $[X_{k,i}]$.

6. The method as claimed in claim 4 wherein the impulse response matrix $[X_i]$ for each heat generating component comprises an (N×1) matrix that describes a sample period of $N \cdot \Delta t$ where $\Delta t$ is the sampling interval.

7. The method as claimed in claim 6 wherein N is greater than or equal to the number of values of the impulse response matrix having the largest number of values.

8. The method as claimed in claim 1 wherein the blood glucose measuring device further comprises a mobile communications module.

9. A blood glucose measuring device comprising:
a plurality of heat generating components;
a measurement strip port operable to receive a removable measurement strip having a reaction site for receiving a blood sample;
a temperature measuring element operable to measure an internal temperature $T_{sensor}$ of the blood glucose measuring device and provide an internal temperature signal that corresponds with the measured internal temperature $T_{sensor}$; and
a controller operable to receive the internal temperature signal from the temperature measuring element and to determine a temperature estimate of the reaction site $T_{site}$ based on blood glucose measuring device usage by applying a dynamic thermal model, wherein:

the dynamic thermal model determines a total temperature elevation $E_{total}$ based at least on part on an activation initiation time, an activation duration time and a thermal magnitude Qx of each heat generating component within a sample period; and
the controller calculates the temperature estimate of the reaction site $T_{site}$ by subtracting the total temperature elevation $E_{total}$ from the internal temperature $T_{sensor}$ provided by the internal temperature signal.

10. The blood glucose measuring device as claimed in claim 9 wherein the dynamic thermal model determines a temperature elevation Ex for each heat generating component by summing a succession of heat impulse responses that are defined at least in part by the activation initiation time, the activation duration time and the thermal magnitude Qx of the heat generating component.

11. A blood glucose measuring device as claimed in claim 10 wherein the dynamic thermal model determines a temperature elevation Ex for each heat generating component such that:

$$[Ex_i] = Qx \cdot [U] \cdot [X_i];$$

where:
- $[Ex_i]$ is a temperature elevation matrix of a heat generating component for times $t_1$ through $t_{Nx}$;
- Qx is the thermal magnitude of a heat generating component;
- [U] is a unit impulse matrix; and
- $[X_i]$ is the impulse response matrix of a heat generating component.

12. A blood glucose measuring device as claimed in claim 9 wherein:
the dynamic thermal model determines a temperature elevation Ex for each of the heat generating components, wherein the temperature elevation Ex for each of the heat generating components is determined at least in part by an impulse response matrix $[X_i]$ for times $t_1$ through $t_{Nx}$, the activation initiation time, the activation duration time and the thermal magnitude Qx for each of the heat generating components; and
the dynamic thermal model determines a total temperature elevation $E_{total}$ of the glucose measuring device by summing the temperature elevation Ex of the heat generating components.

13. A blood glucose measuring device as claimed in claim 12 wherein the blood glucose measuring device further comprises a non-volatile memory configured to store the impulse response matrix $[X_i]$ for each heat generating component such that each impulse response matrix $[X_i]$ is accessible by the controller.

14. A blood glucose measuring device as claimed in claim 12 wherein the impulse response matrix $[X_i]$ for each heat generating component comprises an (N×1) matrix that describes a sample period of $N \cdot \Delta t$ where $\Delta t$ is the sampling interval.

15. A blood glucose measuring device as claimed in claim 14 wherein N is greater than or equal to the number of values of the impulse response matrix having the largest number of values.

16. A blood glucose measuring device as claimed in claim 9 wherein the controller is further operable to determine the activation initiation time, the activation duration time and the thermal magnitude Qx of each heat generating component.

17. A blood glucose measuring device as claimed in claim 9 wherein the blood glucose measuring device is implemented into a mobile communications device, a personal computer or a personal data assistant.

18. A blood glucose measuring device comprising a controller, a temperature measuring element, a measurement strip port, and a plurality of heat generating elements, wherein:
- the measurement strip port is operable to receive a removable measurement strip having a reaction site positioned at an end;
- the temperature measuring element is in electrical communication with the controller and is operable to measure the temperature of the blood glucose measuring device and transmit a temperature signal corresponding to the temperature of the blood glucose measuring device to the controller; and
- the controller is programmed to:
  - determine one or more activity characteristics within a sample period for each of the heat generating components wherein:
    - the one or more activity characteristics comprises an initiation time when a heat generating element becomes active, how long a heat generating element had been active within a sample period, and a thermal magnitude at which a heat generating element had been active within the sample period;
  - calculate a total temperature elevation within the blood glucose measuring device due to the activity characteristics of the heat generating elements within the sample period; and
  - calculate a temperature estimation of the reaction site by subtracting the total temperature elevation from the temperature of the blood glucose measuring device corresponding to the temperature signal received from the temperature measuring element.

19. A blood glucose measuring device as claimed in claim 18 wherein:
- the blood glucose measuring device further comprises a non-volatile memory;
- the controller is further programmed to calculate the temperature elevation of the blood glucose measuring device by performing a linear superposition of a plurality of temperature elevations corresponding to the heat generating components; and
- the controller is further programmed to determine the temperature elevation for each of the heat generating components by performing a linear superposition of a succession of heat impulse responses for each heat generating component, wherein the succession of heat impulse responses is defined by the activity characteristics for each heat generating component within the sample period.

* * * * *